United States Patent
Marsh et al.

(10) Patent No.: US 10,251,611 B2
(45) Date of Patent: Apr. 9, 2019

(54) FREEZING OF GAIT CUE APPARATUS

(75) Inventors: Rodney Ian McLeod Marsh, Eight Mile Plains (AU); Richard Billett, Eight Mile Plains (AU); Duncan Gilmore, Eight Mile Plains (AU); Lydia Kay Goh, Eight Mile Plains (AU); Raymond Lindsay Hope, Eight Mile Plains (AU); Michael Steven McCallion, Eight Mile Plains (AU); Ben McGarry, Eight Mile Plains (AU); James Robert Ward, Eight Mile Plains (AU)

(73) Assignee: Bright Devices Group Pty Ltd, Eight Mile Plains, Queensland (AU)

( * ) Notice: Subject to any disclaimer, the term of this patent is extended or adjusted under 35 U.S.C. 154(b) by 575 days.

(21) Appl. No.: 14/124,752

(22) PCT Filed: Jun. 12, 2012

(86) PCT No.: PCT/AU2012/000669
§ 371 (c)(1),
(2), (4) Date: Apr. 30, 2014

(87) PCT Pub. No.: WO2012/167328
PCT Pub. Date: Dec. 13, 2012

(65) Prior Publication Data
US 2014/0249452 A1    Sep. 4, 2014

(30) Foreign Application Priority Data

Jun. 10, 2011   (AU) .................................. 2011902303

(51) Int. Cl.
*A61B 5/00*   (2006.01)
*A61B 5/11*   (2006.01)
(Continued)

(52) U.S. Cl.
CPC ............ *A61B 5/7282* (2013.01); *A61B 5/112* (2013.01); *A61B 5/4082* (2013.01);
(Continued)

(58) Field of Classification Search
CPC ...... A61B 5/4528; A61B 5/1071; A61B 5/103
(Continued)

(56) References Cited

U.S. PATENT DOCUMENTS

| 5,575,294 A | 11/1996 | Perry et al. |
| 2003/0088294 A1 | 5/2003 | Gesotti |

(Continued)

FOREIGN PATENT DOCUMENTS

WO   2005020866   3/2005

OTHER PUBLICATIONS

Search Report received in corresponding PCT Application PCT/AU2012/000669, dated Aug. 9, 2012.
(Continued)

*Primary Examiner* — Daniel L Cerioni
(74) *Attorney, Agent, or Firm* — Blank Rome LLP

(57) ABSTRACT

A freezing of gait cue apparatus that provides a visual cue, and a method for providing a visual cue, upon detection of a gait irregularity. The gait irregularity, such as a freeze of gait (FOG) for sufferers of neurological diseases like Parkinson's disease, is determined by a processor in communication with a motion sensor worn by the sufferer. When the gait irregularity is determined the apparatus projects a laser light beam on the ground in front of the user of the apparatus to cue them to continue walking.

15 Claims, 5 Drawing Sheets

(52) U.S. Cl.
CPC ............ *A61B 5/6804* (2013.01); *A61B 5/742* (2013.01); *A61B 5/7257* (2013.01)

(58) Field of Classification Search
USPC ........................................................ 600/595
See application file for complete search history.

(56) References Cited

U.S. PATENT DOCUMENTS

| | | | |
|---|---|---|---|
| 2006/0025836 A1* | 2/2006 | Van Gerpen | A61H 3/00 607/88 |
| 2009/0030350 A1 | 1/2009 | Yang et al. | |
| 2010/0274304 A1* | 10/2010 | Wang | A61B 5/112 607/3 |
| 2011/0037419 A1* | 2/2011 | Hoffman | H05B 37/0209 315/313 |
| 2013/0014790 A1* | 1/2013 | Van Gerpen | A61H 3/04 135/66 |

OTHER PUBLICATIONS

"A Wearable System to Assist Walking of Parkinson's Disease Patients: Benefits and Challenges of Context-triggered Acoustic Cueing," Marc Bachlin, et al., Methods Inf Med 2010; 49: 88-95, doi: 10.3414/ME09-02-0003, (c) Schattauer 2010, 8 pages.

"Online Detection of Freezing of Gait in Parkinson's Disease Patients: A Performance Characterization," Marc Bachlin, et al., Body Nets '09 Apr. 1-3, 2009 Los Angeles, CA, USA Copyright 2009 ICST-9799-41-7, 8 pages.

* cited by examiner

FREEZING OF GAIT CUE APPARATUS

FIELD OF THE INVENTION

The invention relates to a freezing of gait cue apparatus. In particular, the invention relates, but is not limited, to an apparatus that provides a cue when a freezing of gait occurrence, such as those associated with neurological diseases like Parkinson's disease, is detected.

BACKGROUND TO THE INVENTION

Reference to background art herein is not to be construed as an admission that such art constitutes common general knowledge in Australia or elsewhere.

Gait irregularities, such as freezing of gait (FOG) or akinesia, can occur in people who suffer from neurological diseases such as Parkinson's disease, cerebral palsy, and multiple sclerosis. Particularly for sufferers of Parkinson's disease, gait irregularity typically occurs when walking in familiar surroundings and in tight corners or doorways, and typically occurs as a brief unexpected inability to walk. This not only interrupts daily life, but often causes accidents, such as falls.

Research has found that providing a cue, such as an audible or visual cue, can assist in handling, or even overcoming, gait irregularities, in particular freezes of gait. Some devices have been developed that provide cues to aid in overcoming gait irregularities. Typically the devices are turned on, either manually or automatically when motion is detected, and provide continual cues, such as a repetitive sound to assist with regular gait. For example, a metronome type sound may be provided to a patient, typically by an earpiece or small speaker, and the patient utilises the sound to maintain a regular gait. More advanced devices may detect the speed and rhythm of a user and adapt the cues to suit their normal gait.

Unfortunately these devices either only provide the feedback when activated, e.g. when a button is pressed, or the like, or continually provide the feedback until disabled. Both of these systems have disadvantages. For a device which only provides feedback when activated, the user must be aware of the gait irregularity and activate it. This may be difficult, particularly if they have akinesia in their arms or hands, and the cue may not be activated and utilised in time to prevent an accident. In the latter case, of continually providing a cue, the user may be self conscious about how the cue affects those around them, as it may intrude upon others, and they may become accustomed to the cue, meaning it loses effectiveness when really required.

Another disadvantage of known devices is that they often include various pieces which need to be arranged in a particular manner. The pieces are typically corded which can interfere with the user's movement, clothes, accessories, or the like. Furthermore, arranging more than one piece on a user is time consuming and, if arranged incorrectly, the device may fail to be effective, or even not work at all.

OBJECT OF THE INVENTION

It is an aim of this invention to provide a freezing of gait cue apparatus which overcomes or ameliorates one or more of the disadvantages or problems described above, or which at least provides a useful alternative.

Other preferred objects of the present invention will become apparent from the following description.

SUMMARY OF INVENTION

According to a first aspect of the invention, there is provided an apparatus for providing a visual cue upon detection of a gait irregularity of a user, the apparatus comprising:
  a processor;
  at least one motion sensor in communication with the processor; and
  a light source in communication with the processor;
  wherein the processor determines a gait irregularity utilising data communicated from the motion sensor and, when a gait irregularity is determined, activates the light source.

Preferably the processor determines the gait irregularity by performing a fast Fourier transform (FFT) on the data from the motion sensor. Preferably the FFT output is separated into predetermined frequency bands. Even more preferably, the FFT output is separated into three predetermined frequency bands, namely low frequency, mid frequency, and high frequency. Preferably the processor determines the gait irregularity by comparing the ratio of the average amplitude of high frequency FFT output to the average amplitude of low frequency FFT output with a predetermined sensitivity number. Preferably the predetermined sensitivity number is in the range of 1 to 20, and even more preferably in the range 3 to 11. The predetermined sensitivity number utilised to determine a gait irregularity may be selected as a result of a user adjusting the sensitivity of the device.

Preferably the apparatus further comprises a housing containing the at least one motion sensor, the light source, and the processor. Preferably the motion sensor is in communication with the processor by being connected to an input of the processor and preferably the light source is in communication with the processor by being connected to an output of the processor.

Preferably the light source includes a laser light source. Preferably the light source is continuous. The light source is preferably activated for a length of time being the greater of a predetermined minimum time span and the length of time the gait irregularity is determined to last for. Preferably the light source projects a light onto a surface adjacent the user. Even more preferably the light source projects a dot, a line, and/or a pattern onto the ground adjacent the user. Preferably the light source projects onto a surface that is in front of the user, even more preferably between 0.5 m to 4 m in front of the user, and even more preferably between 1 m to 2 m in front of the user.

Preferably the orientation of the device is determined by the processor and the light source, preferably a laser, is deactivated, if active, when the apparatus is at certain orientations. Preferably the certain orientations include orientations where the laser would be projected above a horizontal plane.

The direction of projection of the light may be controlled. Preferably the direction is controlled by the processor and, thereafter, by mechanical means. The control of the direction of projection may be in response to signals received from the at least one motion sensor. Preferably, the direction of projection of the light is controlled to project the light at, or at least near, a predetermined distance from the user.

Preferably the motion sensor and light source are connected electrically to the processor. The processor preferably includes a signal processor and, even more preferably, comprises a microcontroller. The at least one motion sensor may comprise one or more accelerometers, gyroscopes, or other motion sensing devices. The microcontroller is preferably programmed to analyse at least one signal from the at least one motion sensor connected to an input of the microcontroller, and determine when a gait irregularity commences.

The microcontroller is also preferably programmed to, upon determining commencement of a gait irregularity, output a signal which, directly or indirectly, activates the light source. One or more different types of gait irregularities may be determined by the processor. Preferably, the processor at least determines between normal walking and a freeze of gait (FOG) episode. The apparatus may further comprise a charging circuit, a power switch, an indicator light, and/or a display. The charging circuit, indicator light and/or display are preferably connected to, and controlled by, the microcontroller.

The charging circuit preferably includes a charging port, for receiving a power source, and a power storage device, preferably a battery. The charging circuit may also include power generators such as, for example, kinetic or solar power generators. The charging port may use a known interface such as, for example, USB.

A data communication system may also be provided for downloading data to or from the apparatus. For example, the processor may record data in use which may subsequently be downloaded to a computer for analysis. The processor preferably logs data output from the motion sensor, preferably in three dimensions in x, y, and z axes. The logged motion data may be downloaded and analysed at a later date.

The data communication system may include a wireless interface, such as Bluetooth, or may include a wired interface, such as USB. The data communication system may utilise the charging port as a multipurpose interface. Additionally, or alternatively, data may be stored on removable memory such as, for example, an SD memory card.

The housing preferably contains the at least one motion sensor, the light source, and the processor within. An aperture may be provided to allow the light source to project from inside the housing. Alternatively, a transparent window may be provided that allows the light to be projected therethrough. According to a form of the invention, the housing is preferably smaller than a 100 mm cube, more preferably smaller than a 50 mm cube, and even more preferably no greater than 50 mm×40 mm×25 mm. The housing preferably has openings for a charging port, power switch, and/or indicator light.

The apparatus preferably includes a wearable element. The wearable element is preferably mounted to the housing and enables the apparatus to be worn by the user. In a preferred form the wearable element is a belt clip. The belt clip preferably has a ball and socket joint. Alternatively, the wearable element may comprise a strap, Velcro, a pin, or the like.

The apparatus preferably allows manual control. Preferably the manual control can be activated in response to a manual control signal. Preferably more than one manual control signals are provided to at least (i) turn the light source on for a predetermined period of time, preferably between 1 and 10 seconds, more preferably between 2 and 5 seconds, most preferably approximately 3 seconds; (ii) turn the light source on until turned off; and/or (iii) turn the light source off if it is turned on. Preferably the manual control signals comprise tapping the housing of the apparatus. Preferably the processor determines when the housing of the apparatus has been tapped by analysing the motion sensor data.

According to a second aspect of the invention, there is provided a method for providing a visual cue upon detecting a gait irregularity of a user, the method comprising:

receiving data from a motion sensor worn by the user;
determining a gait irregularity on a processor using the data received from the motion sensor; and
activating a light source when the gait irregularity is determined.

The processor, motion sensor, and light source are preferably located within a housing, and the housing is preferably affixed to the user, such as attached to an article of clothing. In a preferred form, the housing, with processor, motion sensor, and light source located inside, has a belt clip which can be worn on a belt of the user.

The step of activating the light source preferably comprises activating the light source when a signal is output from the processor. This may occur automatically as a result of the processor outputting the signal when a gait irregularity is determined. For example, the light source may be connected directly to an output of the processor and the signal may be a toggle which turns the light source on and off.

The method may further comprise the step of projecting the light source onto a surface. The step of projecting the light source onto a surface may include directing the light source, wherein directing the light source preferably comprises controlling the direction of projection in response to the data received from the motion sensor. Preferably, the direction of projection of the light is controlled to project the light at, or at least near, a predetermined distance from the user.

The method preferably further comprises the step of deactivating the light source after the later of a predetermined minimum time span and the length of time the processor determines the gait irregularity to last for.

According to a third aspect of the invention, there is provided an apparatus for providing a stimulus upon detection of a gait irregularity of a user, the apparatus comprising:
  a processor;
  at least one motion sensor in communication with the processor;
  a deep brain stimulator in communication with the processor; and
  a housing containing the at least one motion sensor and the processor;
  wherein the processor determines a gait irregularity utilising data communicated from the motion sensor and, when a gait irregularity is determined, communicates with the deep brain stimulator.

Further features and advantages of the present invention will become apparent from the following detailed description.

BRIEF DESCRIPTION OF THE DRAWINGS

By way of example only, preferred embodiments of the invention will be described more fully hereinafter with reference to the accompanying figures, wherein.

DETAILED DESCRIPTION OF THE DRAWINGS

Figure 1:
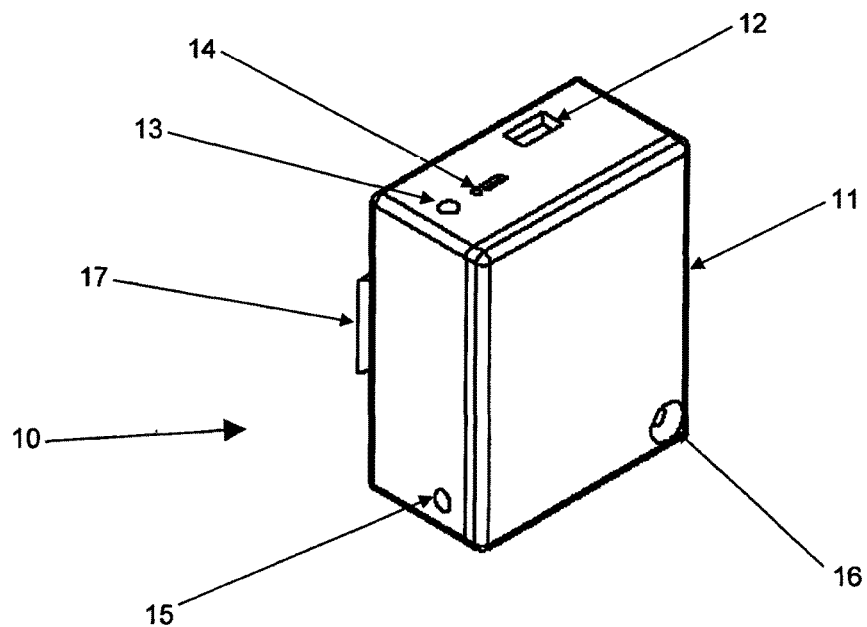
FIG. 1 illustrates a perspective view of an apparatus according to an embodiment of the invention.
Figure 2:
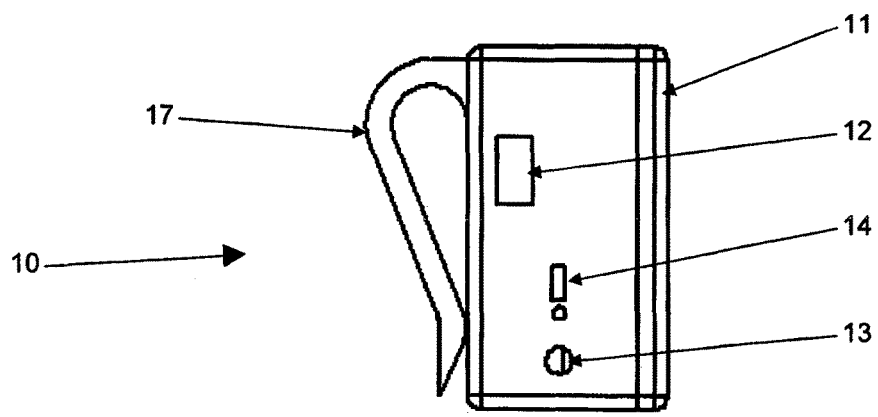
FIG. 2 illustrates a side elevation view of the apparatus illustrated in FIG. 1.

An apparatus 10 according to a preferred embodiment of the invention is illustrated in FIGS. 1 and 2. The apparatus 10 has a housing 11 that contains electronics (shown in FIG. 3) including at least a processor 100, a motion sensor 110, and a light source in the form of a laser 120. The electronics also include a power circuit 130 that powers the electronics, typically utilising a battery for power storage and peripherals 140, such as a power switch, an indicator light, and the like.

The housing 11 in the illustrated embodiment is 50 mm×40 mm×25 mm, and has a charging port 12, an indicator light 13, and a power switch 14 in one side thereof. The housing also has an aperture 15 which the internal laser can project through. Finally, the housing has a countersunk screw hole 16 for fastening parts of the 11 housing together and a wearable element in the form of a belt clip 17 (more clearly visible in FIG. 2). The clip 17 preferably includes a ball and socket joint to allow the user to direct the device in a particular direction, for example to direct the laser a preferred distance from the user.

Figure 3:
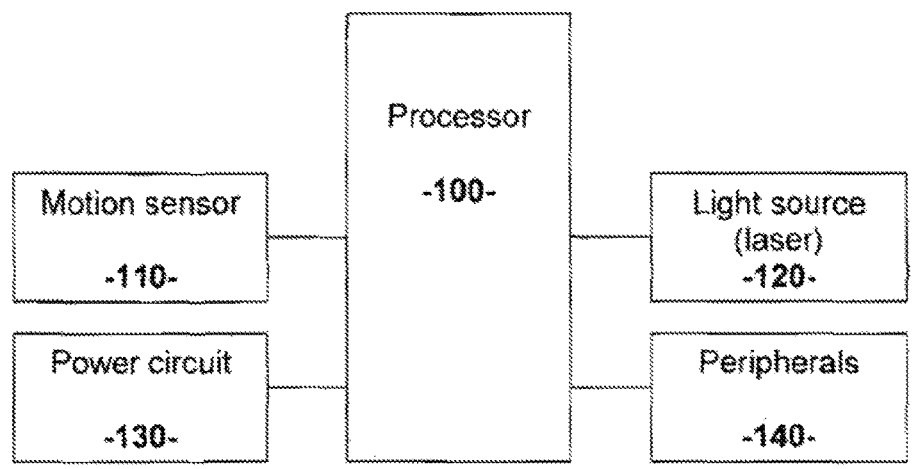
FIG. 3 is a block diagram illustrating components connected to a processor according to an embodiment of the invention.

FIG. 3 illustrates connections between the processor 100 and the motion sensor 110, light source 120, power circuit 130, and any peripherals 140. The motion sensor 110 is connected to an input of the processor and the laser 120 is connected to an output of the processor. The power circuit 130 is connected to power terminals of the processor 100 and, if needed, to the motion sensor 110, light source 120, and/or peripherals 140 as well. The peripherals include the power switch and indicator light which are typically respectively connected to an input and output of the processor.

Figure 4:
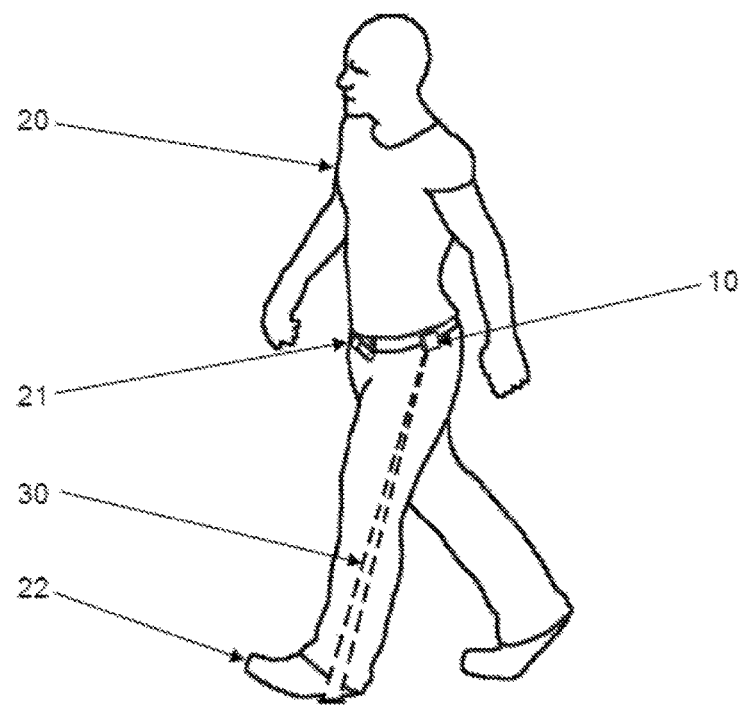
FIG. 4 illustrates an example of an apparatus according to an embodiment of the invention being worn by a user.
Figure 5:
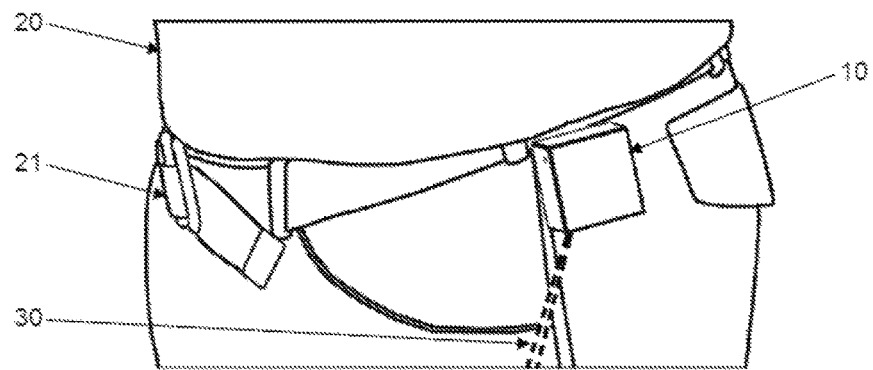
FIG. 5 illustrates a close up view of the apparatus being worn by the user illustrated in FIG. 4.

FIGS. 4 and 5 illustrate the apparatus 10 being worn by a user 20. The user 20 has a belt or waistband 21 which the belt clip 17 mounts onto. When the laser 120 is activated, a light beam 30 is projected from the aperture 15 of the housing towards the ground adjacent feet 22 of the user 20. The direction of projection of the light beam 30 is preferably controlled by the processor, using the motion sensor 110 as an input, to ensure the light beam 30 is directed effectively even during motion.

In use, the apparatus is mounted, by the belt clip 17, on a belt 21 being worn by a user 20. When switched off, the apparatus 10 sits unobtrusively on the belt and should have little to no affect on the user 20. When turned on, the motion sensor 110 of the apparatus starts to detect movements and outputs data regarding the movements to the processor 100. The processor 100 then uses a gait analysis algorithm to differentiate between normal walking and a gait irregularity such as a freeze of gait (FOG).

Figure 6:
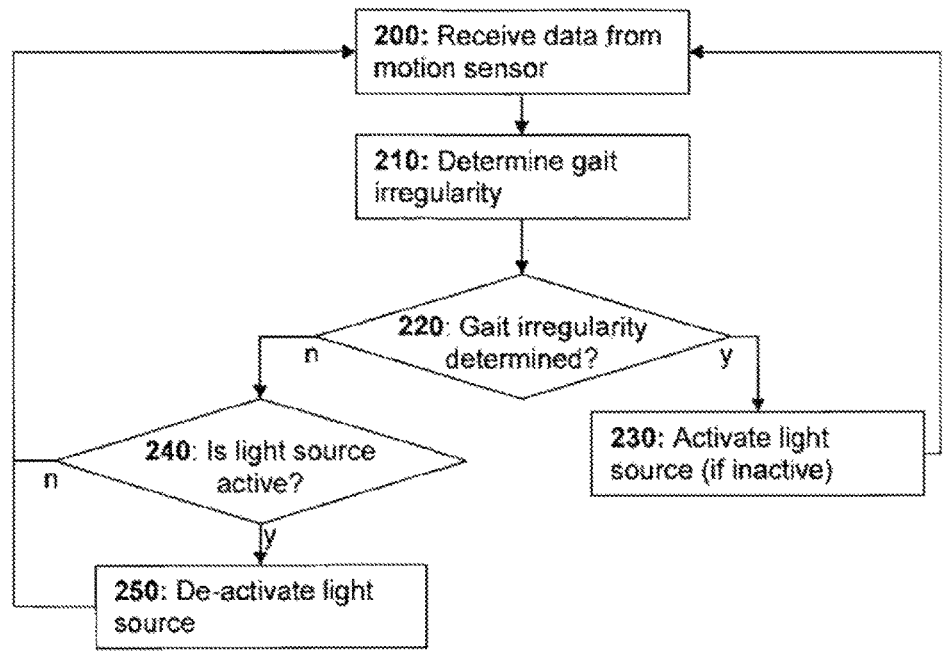
FIG. 6 is a flow chart illustrating steps according to an embodiment of the invention.

FIG. 6 shows a flow chart of a method for providing a visual cue upon detecting a gait irregularity of the user 20. The steps are conducted on the processor 100 which receives data from the motion sensor 110 (step 200) and determines gait irregularities (step 210). If a gait irregularity is determined (at 220) then the light source, laser 120, is activated (step 230). If no gait irregularity is determined (step 220) then the light source, laser 120, is de-activated (step 250) if active (step 240) and the processor 100 continues to receive data from the motion sensor 110 (step 200) and determine whether a gait irregularity occurs (step 210).

Figure 7:
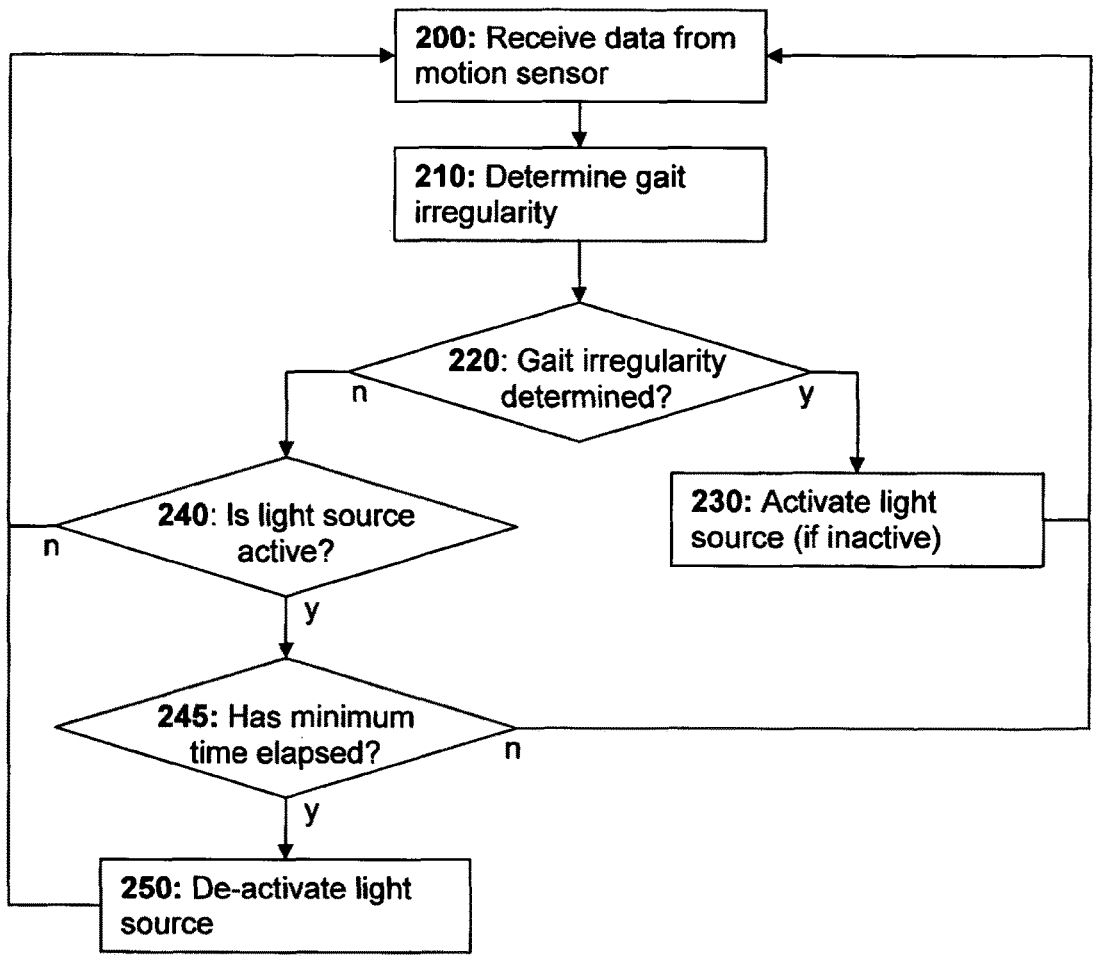
FIG. 7 is a flow chart illustrating steps according to another embodiment of the invention.

FIG. 7 shows a flow chart with an optional minimum cue step. The initial steps are the same but, before de-activating the light source (step 250), the processor 100 determines with a predetermined minimum time has elapsed since detection of a gait irregularity (step 245). If the predetermined minimum time has not yet elapsed then the light source, laser 120, is not yet de-activated (step 250) but rather the processor continues to determine gait irregularities (step 220). Alternatively, if the predetermined minimum time has elapsed (step 245), the light source, laser 120, is deactivated (step 250) and the processor continues to receive data from the motion sensor 110 (step 200) and determine whether a gait irregularity occurs (step 210).

Figure 8:
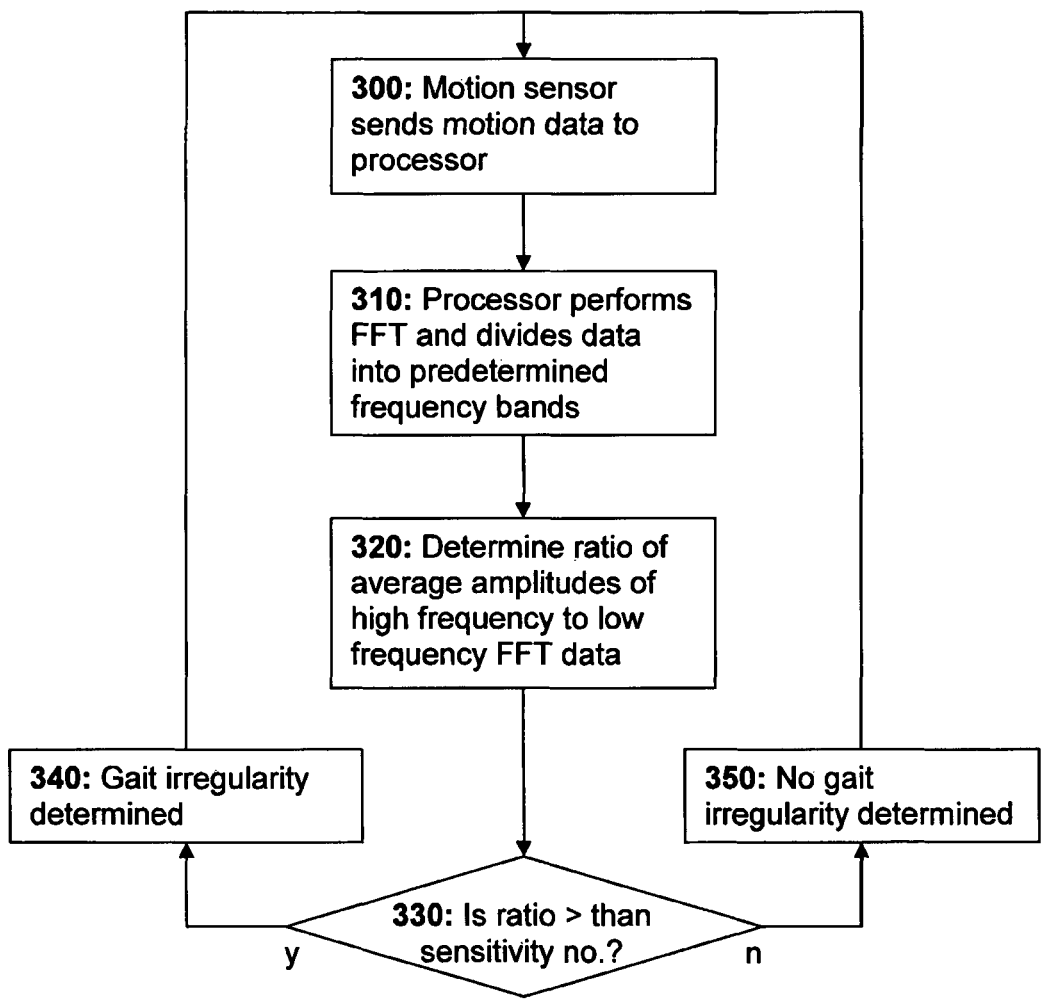
FIG. 8 is a flow chart illustrating steps of determining a gait irregularity.

FIG. 8 shows a flow chart of a method of determining a gait irregularity. First, the motion sensor sends motion data to the processor 100 (step 300). The processor 100 performs a fast Fourier transform (FFT) on the motion sensor data and divides it into predetermined frequency bands (step 310), namely a low frequency band, a mid frequency band, and a high frequency band. The low frequency band relates to walking, the high frequency band relates to a gait irregularity, and the mid frequency band separates the high and the low frequency bands to avoid false readings.

The processor then determines a ratio of the average amplitude in the high frequency band to the average amplitude in the low frequency band (step 320). The ratio is compared with a predetermined sensitivity number (step 330) and if the ratio is greater than the predetermined sensitivity number, the processer determines that a gait irregularity has occurred (step 340). Alternatively, if the ratio is less than the predetermined sensitivity number, the processor determines that no gait irregularity has occurred (step 350). The predetermined sensitivity number may be selected, and adjusted if necessary, to provide a suitable sensitivity for the user 20 wearing the apparatus 10, but is typically within the range 3 to 11.

The processor 100 is optionally configured to record and log motion sensor data when in use. The apparatus 10 then has a data communication system, preferably using a USB interface, for downloading the logged data from the apparatus. The logged data is preferably accelerometer data in three dimensions in x, y, and z axes. This logged motion data can then be downloaded and analysed at a later date, for example by a practitioner to understand the behaviours of a patient or even by a technical support provider to analyse and troubleshoot faults.

From the perspective of the user, when a gait irregularity occurs the apparatus 10 activates the laser 120 which projects a light beam 30 near the feet 22 of the user 20. The projected light beam 30 provides a visual cue to assist the user 20 in overcoming the gait irregularity. Once the gait irregularity is overcome, and optionally after a predetermined minimum time span from when the gait irregularity was determined, the laser 120 is deactivated.

The apparatus 10 has several convenience and safety features.

The sensitivity of the apparatus 10, i.e. the sensitivity which determines when to activate the laser 120, is adjustable. This may be selected by a user, or be adjustable internally, and is effected by adjusting the predetermined sensitivity number used for determining when a gait irregularity occurs. Furthermore, the apparatus 10 has a sleep function to prolong battery life. The sleep function may be activated automatically after no movement over a period of time. The sleep function may also be deactivated (i.e. the device is 'woken') automatically upon sensing movement.

The orientation of the apparatus 10 can be determined by the processor and the processor automatically deactivates the laser 120 when the device is rotated upside down such that the laser 120 would be projected above horizontal. This automatic deactivation significantly prevents the possibility of the laser 120 being directed inappropriately, such as into someone's eyes.

The apparatus 10 can also be controlled manually, such as to manually turn on the laser 120 even when a gait irregularity is not determined. This feature is preferably effected by tapping the housing 11. The motion sensor 110 records movement caused by the tapping and the processor 100 is able to determine when the housing 11 has been tapped and even how many times it was tapped.

In a preferred embodiment, a single tap on the housing 11 turns the laser 120 on for a predetermined period of time, preferably 3 seconds. After that predetermined period of time the apparatus 10 reverts to usual automatic operation. A double tap on the housing 11 turns the laser 120 on permanently until disabled, which may be done through another double tap or similar.

Advantageously, the apparatus 10 is a relatively small and unobtrusive. The light beam 30 can provide the necessary cue to assist a user with a gait irregularity to overcome, or at least manage, the irregularity. Furthermore, since all of the components of the apparatus are co-located within the housing 11, the apparatus 10 is easy to operate and, importantly, is easily put on or removed by the user when desired.

Because the light beam 30 is not permanently active (e.g. pulsing) the user also does not become accustomed to seeing the cue and, accordingly, significantly reduces any immunity to the cues developed through prolonged use. Additionally, because the cue is activated automatically upon detection of a gait irregularity, the user is not required to try to activate the cue when they sense there is a gait irregularity. This prevents the user being concerned with having to activate the cue at a time when they are likely anxious, and ensures that a cue is provided for gait irregularities which the user may not have realised a gait irregularity was occurring or thought that the start of a gait irregularity wasn't of importance until too late.

In an alternative embodiment, the light source is replaced by a deep brain stimulator which can provide deep brain stimulation (DBS) to the user. Similarly to the light source, the deep brain stimulator is activated upon detection of a gait irregularity. The deep brain stimulator is preferably configured to provide necessary stimulation to the brain to assist the user with overcoming the gait irregularity.

In this specification, adjectives such as first and second, left and right, top and bottom, and the like may be used solely to distinguish one element or action from another element or action without necessarily requiring or implying any actual such relationship or order. Where the context permits, reference to an integer or a component or step (or the like) is not to be interpreted as being limited to only one of that integer, component, or step, but rather could be one or more of that integer, component, or step etc.

The above description of various embodiments of the present invention is provided for purposes of description to one of ordinary skill in the related art. It is not intended to be exhaustive or to limit the invention to a single disclosed embodiment. As mentioned above, numerous alternatives and variations to the present invention will be apparent to those skilled in the art of the above teaching. Accordingly, while some alternative embodiments have been discussed specifically, other embodiments will be apparent or relatively easily developed by those of ordinary skill in the art. The invention is intended to embrace all alternatives, modifications, and variations of the present invention that have been discussed herein, and other embodiments that fall within the spirit and scope of the above described invention.

In this specification, the terms 'comprises', 'comprising', 'includes', 'including', or similar terms are intended to mean a non-exclusive inclusion, such that a method, system or apparatus that comprises a list of elements does not include those elements solely, but may well include other elements not listed.

The invention claimed is:

1. An apparatus for assisting a user with walking, the apparatus comprising:
    a housing being associated with the user and including:
        a processor;
        at least one motion sensor being operable to sense motion and being in communication with the processor to communicate motion data; and
        a laser being operable to provide a visual cue and being in communication with the processor;
    wherein the processor determines a freezing of gait in the walking gait of the user, wherein to determine the freezing of gait, the processor is configured to:
        accept an acceleration level on each of three orthogonal axes of the user utilising the motion data communicated from the at least one motion sensor,
        perform a fast Fourier transform (FFT) on the motion data;
        determine that an amplitude level on at least one axis from the FFT for a time is above a predetermined level personally chosen and set by the user,
        divide data output from the FFT into frequency bands, namely a high frequency band indicative of a gait irregularity, a mid frequency band, and a low frequency band indicative of walking, the mid frequency band separating the high and low frequency bands,
        determine a ratio of a first average amplitude of the high frequency band to a second average amplitude of the low frequency band, and
        compare the ratio with a predetermined ratio level;
    wherein in response to the ratio being above the predetermined ratio level, the processor is configured to activate the laser to provide the visual cue projected onto ground adjacent the user for assisting the user with walking.

2. The apparatus according to claim 1, wherein the laser projects a dot, a line, and/or a pattern onto the ground adjacent the user.

3. The apparatus according to claim 1, wherein the motion sensor includes an accelerometer.

4. The apparatus according to claim 1, wherein the housing further comprises a wearable element that enables the apparatus to be worn by the user.

5. The apparatus according to claim 4, wherein the wearable element is a belt clip.

6. The apparatus according to claim 1, wherein the processor is configured to detect a manual control signal.

7. The apparatus according to claim 6, wherein the manual control signal is one or more taps by the user of the housing of the apparatus, and wherein the processor detects the one or more taps by analysing the data from the motion sensor.

8. The apparatus according to claim 6, wherein the light is activated when the processor detects a manual control signal.

9. A method for assisting a user with walking, the method comprising:
receiving data from a motion sensor worn by the user;
determining a freezing of gait in the walking gait of the user on a processor using the data received from the motion sensor by:
accepting an acceleration level on each of three orthogonal axes of the user utilising the motion data received from the motion sensor,
performing a fast Fourier transform (FFT) on the motion data from the motion sensor, and
determining that an amplitude level on at least one axis from the FFT for a time is above a predetermined level personally chosen and set by the user and likely to be associated with freezing of gait for that particular user;
dividing data output from the FFT into frequency bands, namely a high frequency band indicative of a gait irregularity, a mid frequency band, and a low frequency band indicative of walking, the mid frequency band separating the high and low frequency bands;
determining a ratio of a first average amplitude of the high frequency band to a second average amplitude of the low frequency band; and
comparing the ratio with a predetermined ratio level; and
in response to the ratio being above the predetermined ratio level, providing a visual cue projected onto ground adjacent the user for assisting the user with walking by activating a laser when the freezing of gait is determined.

10. The method of claim 9, wherein the step of activating the laser when the freezing of gait is determined comprises activating a laser light that projects a dot, a line, and/or a pattern onto the ground adjacent the user.

11. The apparatus of claim 1, wherein the processor determines the freezing of gait including at least one of akinesia in walking and brief inability to walk.

12. The apparatus of claim 1, wherein to determine the freezing of gait, the processor is configured to determine that the first average amplitude of the high frequency band is greater than the second average amplitude of the low frequency band.

13. The method of claim 9, wherein the step of determining the freezing of gait on the processor comprises determining that the first average amplitude of the high frequency band is greater than the second average amplitude of the low frequency band.

14. The apparatus of claim 1, wherein the processor is configured to adjust the predetermined level based on user selection.

15. The method of claim 9, comprising adjusting the predetermined level based on user selection.

* * * * *